United States Patent [19]
Bell et al.

[11] Patent Number: 5,580,527
[45] Date of Patent: Dec. 3, 1996

[54] POLYMERIC LUMINOPHORES FOR SENSING OF OXYGEN

[75] Inventors: Thomas W. Bell, East Setauket; Suresh K. Sahni, Sound Beach; Terje A. Skotheim, Shoreham, all of N.Y.

[73] Assignees: Moltech Corporation, Tucson, Ariz.; The Research Foundation of State University of New York, Albany, N.Y.

[21] Appl. No.: 353,924

[22] Filed: Dec. 12, 1994

Related U.S. Application Data

[63] Continuation-in-part of Ser. No. 191,946, Feb. 4, 1994, abandoned, which is a continuation-in-part of Ser. No. 884,700, May 18, 1992, abandoned.

[51] Int. Cl.⁶ .................................................. G01N 21/64
[52] U.S. Cl. .................... 422/82.07; 422/82.05; 422/82.06; 422/82.08; 422/86; 252/301.26; 252/408.1; 252/600; 526/265; 435/14; 435/25; 436/71; 436/95; 436/98; 436/132; 436/136
[58] Field of Search .................... 252/301.26, 408.1, 252/600; 422/82.05, 82.06, 82.07, 82.08, 82.09, 86, 79; 526/265; 435/14, 25; 436/95, 98, 131–132, 71, 136

[56] References Cited

U.S. PATENT DOCUMENTS

| | | | |
|---|---|---|---|
| 4,224,125 | 9/1980 | Nakamura et al. | 204/403 |
| 4,424,359 | 1/1984 | Kaschig et al. | 546/255 |
| 4,560,534 | 12/1985 | Kung et al. | 422/82.02 |
| 4,568,633 | 2/1986 | Lovecchio et al. | 430/367 |
| 4,581,314 | 4/1986 | Reczek et al. | 430/213 |
| 4,611,890 | 9/1986 | Elliot et al. | 359/265 |
| 4,711,245 | 12/1987 | Higgins et al. | 128/635 |
| 4,711,708 | 12/1987 | Meyer et al. | 204/280 |
| 4,712,865 | 12/1987 | Hsu et al. | 385/12 |
| 5,030,420 | 7/1991 | Bacon et al. | 422/82.07 |
| 5,128,102 | 7/1992 | Kaneko et al. | 422/56 |

FOREIGN PATENT DOCUMENTS

| | | |
|---|---|---|
| 1-155244 | 6/1989 | Japan . |
| 1-280242 | 11/1989 | Japan . |
| 2-190748 | 7/1990 | Japan . |
| 8806287 | 2/1988 | WIPO . |

OTHER PUBLICATIONS

S. M. Nelson et al. *J. Chem. Soc.* 1968, 272–276.
M. Kaneko et al. *J. Polym. Sci. Polym. Lett. Ed.* 1982, 20, 593–597.
J. M. Kelly et al. *Inorg. Chem.* 1983, 22, 2818–2824.
D. H. Grayson et al. *Sol. Energy R & D Eur. Community, Ser. D.* 1983, 2, 51–57.
S. L. Buell et al. *J. Phys. Chem.* 1983, 87, 4675–4681.
P. Bosch et al. *An. Quim., Ser. C* 1985, 81, 162–166.
J. R. Bacon et al. *Anal. Chem.* 1987, 59, 2780–2785.
M. Kaneko et al. *Macromolecules* 1987, 20, 2265–2267.
M. Kaneko et al. *Makromol. Chem.* 1987, 188, 2011–2017.
M. Kaneko et al. *J. Polym. Sci., Polym. Chem. Ed.* 1982, 20, 1011–1019.
J. L. Bourdelande et al. *J. Photochem. Photobio.* 1988, 44A, 51–55.
K. T. Potts et al. *Macromolecules* 1988, 21, 1985–1991.
J. N. Demas et al. *J. Macromol. Sci., Chem.* 1988, A25, 1189–1214.
J. L. Bourdelande et al. *Chem. Abstr.* 1989, 111, 40262d.
K. Hanabusa et al. *Makromol. Chem.* 1990, 191, 391–396.

(List continued on next page.)

*Primary Examiner*—Arlen Soderquist
*Attorney, Agent, or Firm*—Roland Plottel

[57] ABSTRACT

The present invention relates to polymeric luminophores which contain ruthenium, osmium, and rhenium complexes covalently attached to polymer matrices. The polymeric luminophores are capable of having their luminescence quenched by molecular oxygen and may be coated on optical fibers to form sensing elements to detect oxygen in gases and fluids.

7 Claims, 6 Drawing Sheets

OTHER PUBLICATIONS

K. Yamada et al. *Makromol. Chem.* 1990, 191, 2871–2880.

E. R. Carraway et al. *Anal. Chem.* 1991, 63, 337–342.

R. Ramaraj et al. *J. Photochem. Photobiol.* 1991, 56A, 287–293.

M. Kaneko et al. *Makromol. Chem., Macromol. Symp.* 1992, 59, 183–197.

K. Hanabusa et al. *Makromol. Chem.* 1992, 193, 1309–1319.

S. K. Sahni et al. *J. Chem. Soc., Chem. Commun.* 1993, 123–125.

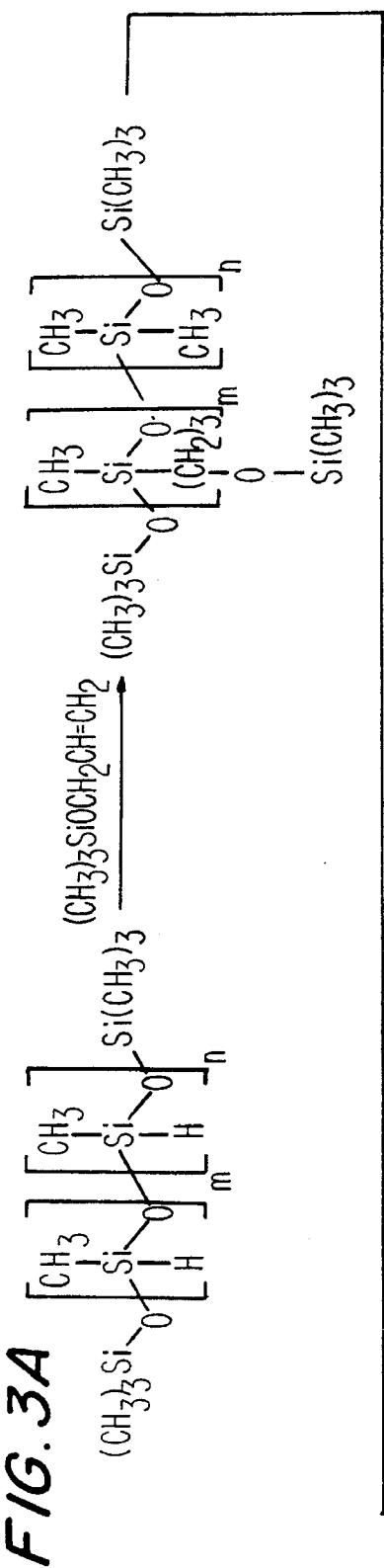
FIG.3A
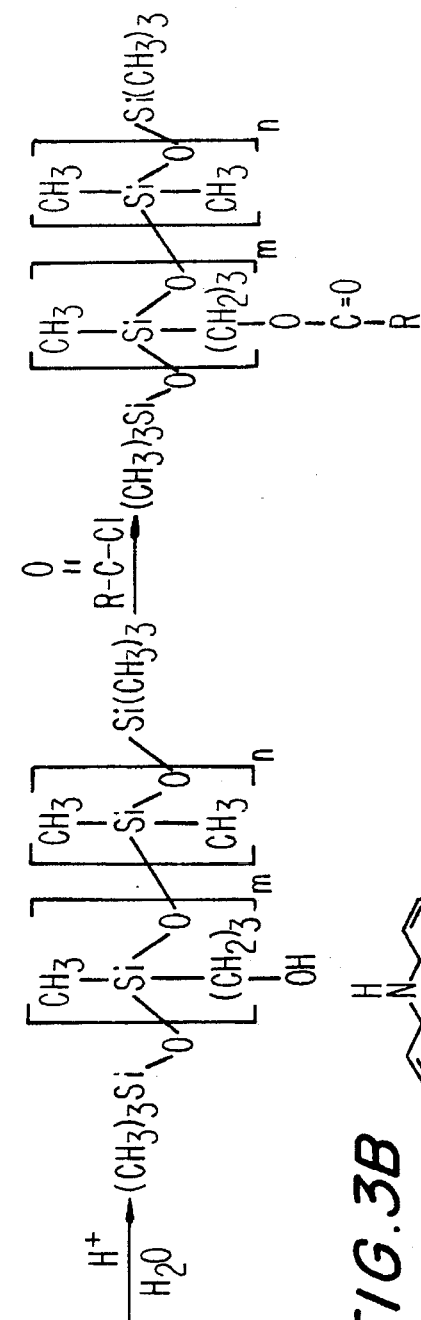
FIG.3B
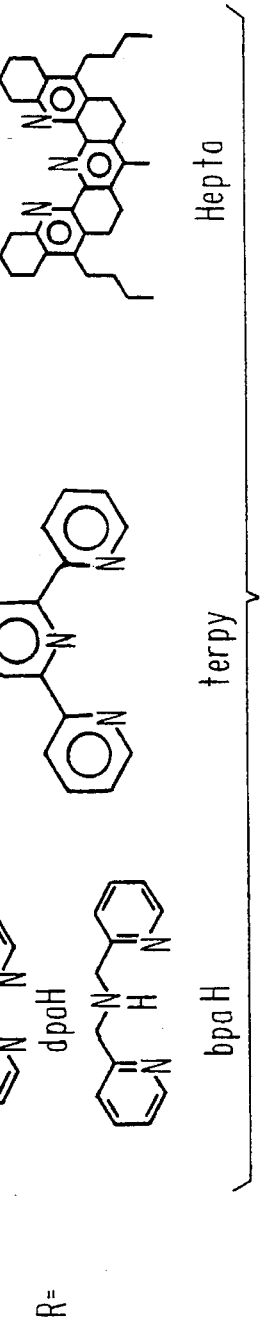

[Ru(2,2'-bipyridine)$_2$(bispicolylamine)]$^{2+}$

[Ru(4,7-diphenylphenanthroline)$_2$(bispicolylamine)]$^{2+}$

POLYMERIC LUMINOPHORES FOR SENSING OF OXYGEN

This application is a continuation-in-part of Ser. No. 08/191,946, filed Feb. 4, 1994, now abandoned, which is a continuation-in-part of Ser. No. 07/884,700, filed May 18, 1992, now abandoned.

Partial support for this invention came from the United States Government through research grants awarded by the National Institutes of Health and the United States Department of Energy. The Government has certain rights in this invention.

BACKGROUND OF THE INVENTION

A large number of transition metal complexes, particularly those of the platinum class of metals with $d^6$ electronic configuration with a class of ligands generally referred to as α-diimines, have unique optical, electrochemical, photochemical and photophysical properties. These properties, which are based on efficient and facile electron-transfer and energy-transfer processes, are responsible for numerous applications in the areas of photocatalysis, electrocatalysis and photoelectrolysis [Kalyanasundram, *Coordination Chemistry Reviews*, 46, 159 (1982); Kalyanasundaram, Gratzel and Pelizzetti, *Coordination Chemistry Reviews*, 69, 57 (1986); Serpone, *Photochemical Energy Conversions*, Elsevier, Amsterdam, 1989; and Collins and Sauvage, *Coordination Chemistry Reviews*, 93, 245 (1989)]. A large number of ruthenium(II) and osmium(II) polypyridine complexes have been synthesized and evaluated for a variety of applications utilizing their photoactive and electroactive properties [Seddon and Seddon, *The Chemistry of Ruthenium*, Elsevier, Amsterdam, 1984; Juris, Balzani, Barigelletti, Campagna, Besler, and Von Zelevsky, *Coordination Chemistry Reviews*, 84, 85 (1988); and Balzani, Juris and Scandola, *Homogeneous and Heterogeneous Catalysis*, Reidel Publishing Corporation, New York, 1990]. Numerous such complexes have been used to prepare chemically-modified electrodes, which can be applied as electrocatalytic and electrochemical sensors (Murray in Bard (ed.), *Electrochemical Chemistry*, Vol. 13, M. Dekker, New York, 1984, p. 1 and Skotheim (ed.), *Handbook of Conducting Polymers*, M. Dekker, New York, 1986). Many of these complexes emit light strongly at room temperature and their luminescence can be quenched by a variety of reagents including molecular oxygen. The luminescence properties of this class of metal complexes enable their use as molecular sensing elements in fiber-optic chemical sensors and biosensors [Wolfbeis, *Fiber-Optic Chemical Sensors and Biosensors*, CRC Press, Boston, 1991]. Fiber-optic chemical sensors (the general term 'sensor' will be used both for chemical sensors and biosensors in this document) offer advantages to electrochemical sensors for monitoring and determining chemical and biochemical analytes. Of various optical methods employed for chemical analysis, those based on luminescence (emission) spectroscopy are considered particularly attractive because of their high sensitivity and specificity. Both inorganic and organic luminescent materials can be used as 'sensing elements', 'molecular probes', 'reporters' or 'indicators' for remote quantification of various physical parameters (e.g. temperature, pH, $pO_2$, and $pCO_2$) and chemical (e.g. ethanol and methanol) and biochemical analytes (e.g. glucose, creatinine and cholesterol).

A variety of metal-organic compounds of a number of transition metals and lanthanides are known to be intensely luminescent. Luminescent transition metal complexes, especially of $d^6$ platinum metals such as ruthenium, osmium, rhenium, rhodium and iridium with α-diimine type ligands (for example, 2,2'-bipyridine, 1,10-phenanthroline, terpyridine and their substituted derivatives) exhibit very desirable features in terms of their optical spectra, excited state lifetimes and luminescence quantum yields, making them very attractive luminophores for fiber-optic sensors. Ruthenium(II) and rhenium(I) carbonyl halide-polypyridine complexes exhibit intense visible absorption, which is important for sensitivity, simplicity of sensor design and adaptability to a variety of excitation sources. Their excited states have long lifetimes and high luminescence quantum yields that are independent of the excitation wavelength. The absorption and emission characteristics of metal-polypyridine complexes can be fine-tuned by varying substituents on the polypyridine ligand or by changing the metal atoms. Fine-tuning of optical, photophysical and redox properties of the metal complexes can provide tailor-made luminophores for fabricating a variety of fiber-optic sensors for environmental, oceanographic, industrial, biotechnological and biomedical applications. For instance, luminescence-based oxygen sensors for oceanographic applications should contain a luminophore whose emission maximum does not lie in the 660–700 nm range, where emission of chlorophyll can interfere with the emission of the molecular probe of the sensor. Oxygen sensors designed for invasive biomedical applications have to take into account the properties of various luminescent materials present in blood, which can interfere with emission signal or quench the luminescent state of the luminophore.

A large number of ruthenium(II), osmium(II) and rhenium(I) carbonyl halide-polypyridine complexes [Sacksteder, Zipp, Brown, Streich and Demas, *Inorganic Chemistry*, 29, 4335 (1990)] exhibit a good combination of desirable properties, making them suitable luminophores in various sensor applications [Demas and DeGraff, *Proceedings SPIE*, 1172, 216 (1989)]. None of these metal-polypyridine complexes are ideal for commercial applications for various reasons, including their tendency for ligand substitution (photolability) and difficulty for chemical immobilization in polymeric matrices. For long-term stability it is essential that the luminophore be chemically immobilized on an insoluble polymeric support through the formation of a covalent bond [Seitz, *CRC Critical Reviews in Analytical Chemistry*, 19, 135, 1988].

Several methods can be employed for immobilization of chemical and biochemical species. The most effective immobilization procedure is one in which a chemical bond is formed between a polymer and the species to be immobilized. Immobilization very often results in attenuation of various characteristics of a reactive species. However, attachment of low molecular weight luminophores to polymeric supports can result in less severe attenuation of vital luminophore characteristics [Carraway, Demas, DeGraff and Bacon, *Analytical Chemistry*, 63, 337 (1991)].

A number of sensing elements [Marsoner, Kroneis and Wolfbeis, European Patent Application, EP 109,959 (1984); Barnikol and Burkhard, German Offen. DE 3,320,752 (1983); Hsu and Heitzmann, U.S. Pat. No. 4,712,865 (1987); Kung, Vogelhut, U.S. Pat. No. 4,560,534 (1985)] and methods, schemes and apparatus [Buckles, PCT International Application 8,100,912 (1981); Bacon and Demas, French Demande FR 2,538,550 (1984); Bacon and Demas, U.S. Pat. No. 5,030,420 (1991); Klainer, Walt and Gottlieb, International Application Number PCT/US88/00041 (1988); Wagner, U.S. Pat. No. 5,001,054 (1991); Higgins, Hill, Plotkin, U.S. Pat. No. 4,711,245 (1987)] have been devised and evaluated. Polymer-catalyst based transducers used by King and Vogelhut for the determination of glucose in whole blood do not make use of platinum metal-polypyridine complexes and are only designed for conductometric measurements. Bacon and Demas [French Demande FR 2,538, 550 (1984) and U.S. Pat. No. 5,030,420 (1991)] described the use of sensing elements based on platinum metal-polypyridine complexes which have no possibility of chemical or covalent attachment to polymeric matrices. These metal complexes could only be used as physical mixtures with polymers, producing inhomogeneous distribution of the sensing elements and rapid leaching of the luminophore into the analyte solution. Wagner [U.S. Pat. No. 5,001,054 (1991)] proposed a method based on the use of a conjugate of glucose and a fluorescent dye coated onto an optical fiber for monitoring the glucose level in body fluid. This sensor is not expected to be durable because the dye is not covalently immobilized. Klainer, Walt and Gottlieb [International Application Number PCT/US88/00041 (1988)] have also described fiber optic sensing devices for measuring chemical or physiochemical parameters of a body fluid or tissue. These devices are based on polymeric photoactive dyes employed as sensing elements for pH and oxygen sensors.

Despite considerable efforts, no metal-organic luminophore has yet demonstrated the possibility of chemical immobilization while maintaining most of their useful optical, photophysical and photochemical characteristics. Chemically immobilized luminophores can be cast in ultrathin films containing evenly distributed sensing material. In fiber-optic sensors for continuous monitoring of chemical and biochemical analytes, the time to establish equilibrium between analyte and sensing element is of crucial importance. Ultrathin films containing immobilized luminophores can be used to produce fiber-optic sensors with very short response times.

Immobilization processes involve two components: (a) polymeric supports and (b) immobilization methods. The choice of polymeric supports is generally governed by its permeability for the analyte, stability, availability, suitability for sensing element immobilization and its compatibility with the sample and various materials used in the fabrication of optrodes [Hodge and Sherrington, *Polymer-supported Reactions*, J. Wiley, New York, 1980 and R. B. Seymour and Marks, *Applications of Polymers*, John Wiley & Sons, New York, 1988]. The choice of the right material is very important because the nature of the polymer has a pronounced effect on sensor performance. For example, the response time is governed by the diffusion coefficients of gases or liquids and the quenching efficiency by the solubility of the gas in the polymer. Among the variety of polymers evaluated for immobilization, siloxanes are unique in having permeability for most gases as well as excellent biocompatibility and optical and mechanical properties [Robb, Thin Silicone Membranes-Their Permeation Properties and Some Applications, *Annals New York Academy of Science*, 146, 119 (1986) and Anderson, Arkles and Larson, *Silicone Compounds Register and Reviews*, Petrarch Systems, Bristol, Pa., 1987]. Numerous silicone polymers are commercially available and allow for easy manufacture of membranes, emulsions, suspensions and coatings. Other hydrophobic polymeric supports include poly(vinyl chloride), poly(ethylene), poly(tetrafluoroethylene) and poly(styrene). Except for poly(styrene), most of other polymers are modified with difficulty. Even polystyrene is not very suitable for immobilization of luminophores, as it can interfere with their luminescence properties. A variety of hydrophilic supports characterized by a large number of hydrogen bonding groups, such as OH or $NH_2$, or by the presence of a number of charged groups such as $COO^-$ or $SO_3^-$ in the polymer chain, are also known. Typical examples include polysaccarides (celluloses), polyacrylates, poly-acrylamides, polyglycols, and a variety of so-called hydrogels. Generally, these polymers are easily penetrated by aqueous solutions and they have limited compatibility with hydrophobic polymers. Several polymeric supports with mixed hydrophilic and hydrophobic groups are also known. Typical examples include ion-exchange materials such as poly(acrylonitrile-methylsulfonate) copolymers, polysulfones, and partially fluorinated polyethylene (Nafion).

Several immobilization techniques are available for combining 'sensing reagents' with polymeric supports [Hodge and Sherrington, *Polymer-supported Reactions in Organic Synthesis*, John Wiley, New York, 1980 and Sharma, Bailey and Messing, Immobilized Bio-materials: Techniques and Applications, *Angew Chemie, International Edition, English Translation*, 21, 837 (1982)]. Three immobilization methods, namely, chemical covalent, physical and electrostatic techniques, are commonly used for the preparation of immobilized sensing molecules. Mechanical or physical immobilization or encapsulation involves adsorption and inclusion of molecules in polymer matrices. This is the simplest and therefore the least expensive way of immobilization. However, in this type of immobilization there is no bonding between the sensing reagent and the polymeric support and the immobilized luminophores can leach out. Electrostatic immobilization uses rigid polymeric supports with charged groups such as sulfonic (sulfonated polystyrene) or quaternized ammonium groups capable of binding electrostatically to molecules of opposite charge. For example, sulfonated polystyrene can bind a variety of cations with varying strength. Numerous ion-exchange materials of varying binding strengths are commercially available [Bishop, *Indicators*, Pergamon Press, New York, 1972; Zhujun and Seitz, *Analytica Chimica Acta*, 160, 47, 1984]. The ease of execution and the degree of reproducibility of electrostatic immobilization is also decreased by non-homogeneous distribution of sensing materials and their bleeding on long-term use.

Current methods for immobilizing luminescent metal complexes in polymer matrices are not adequate for practical applications, such as fiber-optic sensors for oxygen determination. The method of Bacon and Demas [French Demande FR 2,538,550 (1984) and U.S. Pat. No. 5,030,420 (1991)] produces materials in which the luminophore is physically mixed with the polymer matrix. The resulting polymer films lack durability because the luminophore can be leached from the polymer matrix. S. L. Buell, et al. [*J. Phys. Chem.* 1983, 87, 4675–4681] have described electrostatically bonded luminophores combining ruthenium polypyridine complexes with ion exchange resins. While somewhat more durable, these materials are subject to leaching of the luminophore by displacement with ions in the analyte solution. Also, the polymer matrix cannot be varied easily because ion-exchange properties are required for this method of immobilization. Finally, K. T. Potts, et at. [*Macromolec.* 1988, 21, 1985–1991] have described polystyrene copolymers containing covalently bound terpyridyl ligands and $Ru(tpy)_2X_2$ complexes. While these platinum-metal complexes are covalently bound to the polymer matrix, they are not described as luminescent. Low luminescence quantum yields are expected for such materials because of interactions between the excited luminophore and the polystyrene matrix, as mentioned previously. Moreover, polystyrene has inferior physical properties (e.g. permeability and polarity) for sensor applications in aqueous solutions and the polymer matrix cannot be varied easily with this method of luminophore immobilization.

SUMMARY OF THE INVENTION

The invention concerns a class of polymeric luminophores having the structure

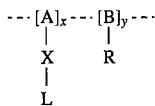

wherein:

—[A]$_x$—[B]$_y$— represents a polymer chain; A and B are independently selected from the group consisting of formulas a to i as follows:

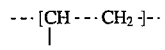   a

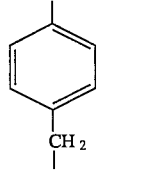   b

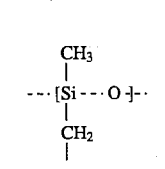   c

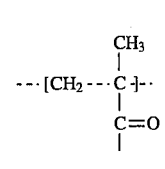   d

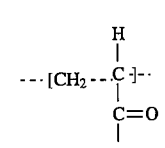   e

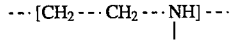   f

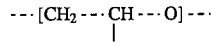   g

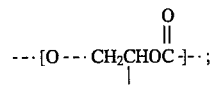   h i

X is selected from the group consisting of —(CH$_2$)$_n$, —(CH$_2$)$_n$CH(OH)CH$_2$— or —(CH$_2$CH$_2$O)$_n$, where n=0–10; L independently represents a luminescent platinum-metal polypyridine complex capable of having its luminescence quenched by the presence of oxygen and selected from the group consisting of the general formulas [M(N,N)$_2$(N,N,N—H)$_2$]Y$_2$, [M(N,N,N—H)$_2$]Y$_2$, [Re(CO)(N,N)(N,N,N—H)Cl], or [Re(CO)$_2$(N,N,N—H)Cl] wherein M=Ru(II) or Os(II), N,N is a bidentate ligand of α,α′-diimine type, and N,N,N—H is a tridentate ligand of the formula P—(CH$_2$)$_s$—NH—(CH$_2$)$_t$—Q, wherein P and Q represent pyridine, quinoline, imidazole, pyrazole or triazole rings or their derivatives and s and t independently have numerical values between 0 and 3; Y is an anion such as Cl, Br, I, PF$_6$, BF$_4$, ClO$_4$, NO$_3$ or NCS; L is covalently bonded to X or directly to the polymer chain by substitution of a hydrogen atom on a nitrogen atom of N,N,N—H; R independently represents hydrogen or an alkyl, aryl or heteroaryl group; and x and y represent the number of monomer units in the polymer structure.

The invention also concerns a chemical process for preparing such polymeric luminophores above by reacting a tridentate ligand of the formula P—(CH$_2$)$_s$—NH—(CH$_2$)$_t$—Q wherein P, Q, R, s and t are defined as above, with a polymer having the structure

wherein, A, B, X, R, x and y are defined as above and Z represents Cl, I, p-toluenesulfonate or methanesulfonate in an appropriate solvent in the presence of a proton acceptor; and then reacting with a presynthesized N-heterocyclic complex selected from the group having the general formulas [M(N,N)$_2$Cl$_2$], [M(N,N,N—H)$_2$]Y$_2$, [Re(CO)$_5$Cl], [Re(CO)$_3$(N,N)Cl] or [Re(CO)$_2$(N,N,N—H)Cl], where M=Ru(II) or Os(II), N,N is a bidentate ligand of α,α′-diimine type and N,N,N—H is a tridentate ligand of the formula P—(CH$_2$)$_s$—NH—(CH$_2$)$_t$—Q, wherein P, Q, R, s and t are defined as above.

This invention also concerns a chemical process for preparing such polymeric luminophores by reacting a luminescent platinum-metal polypyridine complex having the general formula [M(N,N)$_2$(N,N,N—H)]Y$_2$. [M(N,N,N—H)$_2$]Y$_2$, [Re(CO)(N,N)(N,N,N—H)Cl] or [Re(CO)$_2$(N,N,N—H)Cl], where M, N,N, N,N,N—H and Y are defined as above, with a functionalized presynthesized polymer having the structure

wherein A, B, X, R, x and y are defined as above and Z represents Cl, I, p-toluenesulfonate or methanesulfonate in an appropriate solvent in the presence of a proton acceptor.

These new polymeric luminophores exhibit intense absorptions in the UV-visible region, and have attractive photophysical and photochemical properties, including emission spectra, excited state lifetimes and luminescence quantum yields. In addition, these polymeric metal complexes can be synthesized by two different, convenient methods. The metal complexes can be covalently attached to the polymer matrix; alternately, one of the ligands can be attached first to the polymer matrix, then the metal complexes can be formed in a second step. These polymeric luminophores can be cast into thin films or immobilized in an oxygen-permeable membrane and attached to or coated onto optical fibers. The optical fibers bearing these immobilized luminophores can be attached to detecting systems and computers to develop chemical sensors to be used as transducers in biosensors for measuring and monitoring a variety of chemical and biochemical analytes.

OBJECTIVES OF THE INVENTION

It is an object of this invention to provide luminescent materials consisting of platinum metal-polypyridine compounds that are covalently attached to various polymeric matrices.

A further object of this invention is to provide methods for the covalent attachment of luminescent metal complexes to various polymeric matrices.

A further object of this invention is to provide chemically immobilized luminophores whose luminescence can be quenched by molecular oxygen. This quenching phenomenon can be used to measure the concentration of oxygen in gases and fluids.

A further object of this invention is to provide non-leachable, moisture insensitive and heat-insensitive immobilized luminophores.

A further object of this invention is to provide immobilized luminophores whose luminescence is not quenched by ether, chloroform and other gases or materials used in medical practice.

A further object of this invention is to provide immobilized luminophores which can be cast into thin films or coated on a variety of hard, transparent surfaces such as optical fibers or sheets of glass or plastic.

A further object of this invention is to provide methods to use these immobilized luminophores as sensing elements in fiber-optic sensors for oxygen.

A further object of this invention is to provide transducer oxygen optrodes which can be employed as sensing elements for the development of biosensors based on biocatalysts such as oxidases.

It is a further object of this invention to provide immobilized luminophores for oxygen optrodes to be employed as transducers in sensing devices for glucose, creatinine, cholesterol and similar clinical analytes.

These and other benefits of the present invention will be apparent to those skilled in the art from the following description and examples.

BRIEF DESCRIPTION OF THE DRAWINGS

FIG. 3 shows a method used for the covalent attachment of pyridine-type ligands to a polysiloxane.

DESCRIPTION OF THE INVENTION

Figure 1:
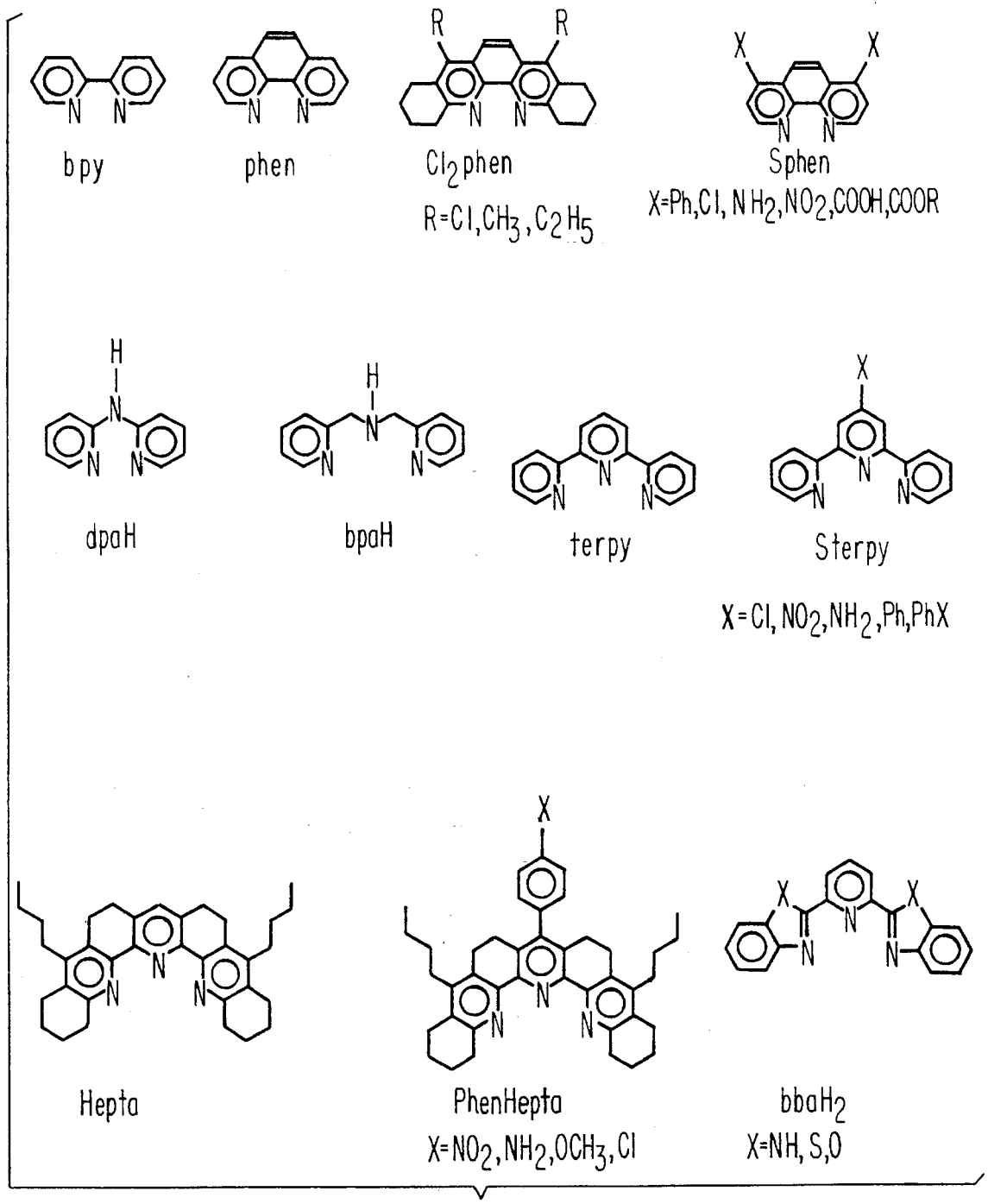
FIG. 1 depicts the structures of some of the ligands used in this invention.

The luminescent platinum metal coordination compounds can be prepared by heating a mixture of [M(N,N)$_2$X$_2$].nH$_2$O with an excess of bidentate or tridentate polypyridine ligand of the type N,N,N—H (e.g. bispicolylamine or 2,2'-dipyridyl amine) in 95% aqueous ethanol or ethylene glycol under nitrogen or argon gas atmosphere. Before heating the mixture, the reaction apparatus is thoroughly flushed with nitrogen or argon gas. The mixture is stirred and heated under nitrogen or argon for ca. 6 to 30 hours. The highly soluble complexes so formed can be isolated by concentrating the reaction mixture under vacuum followed by adding of salts like ammonium hexfluorophosphate or potassium perchlorate. The precipitated complexes are thoroughly washed with water, ethanol and ether and dried under vacuum at room temperature to obtain the complexes of the formulation conforming to [M(N,N)$_2$(N,N,N—H)]X$_2$, where X=PF$_6$, BF$_4$ or KClO$_4$. Hexafluorophosphate salts of these complexes are generally preferred because of their ease of preparation and handling. Perchlorate salts can be shock-sensitive and may sometimes easily explode. If no solid complexes are isolated even after the addition of salts such as ammonium hexafluorophosphate, the reaction mixture is concentrated under vacuum and allowed to cool and slowly evaporate at room temperature, whereupon the solid complexes slowly separate from the reaction mixture.

The rhenium(I) carbonyl halide complexes are synthesized by heating a mixture of Re(CO)$_5$X (X=Cl or Br) and an excess of a polypyridine-type bi- or tridentate ligand discussed above. The solid complexes generally separate from the reaction mixture on cooling to room temperature or standing in a refrigerator. The mixed ligand rhenium(I) carbonyl halide complexes of the type [Re(CO)$_3$(N,N)(N,N,N—H)Cl] are prepared by heating a mixture of toluene, a complex of the type [Re(CO)$_3$(N,N)$_2$Cl] and an excess of a bidentate or tridentate ligand (N,N,N—H) like 2,2'-dipyridyl amine, bispicolylamine or their substituted derivatives. The solid complexes are generally obtained on cooling the reaction mixture to room temperature with or without evaporation or upon standing in a refrigerator. The complexes are purified by thorough washing with n-hexane, ethanol and ether, followed by chromatographic separation on an alumina or Sephadex column.

Chemical immobilization, which involves formation of a covalent bond between a 'sensing reagent' (luminophores in this case) and the polymeric support, is also known as covalent immobilization. Covalent bond formation is considered the best technique for immobilization of both chemical and biochemical species because of the stable and predictable nature of the covalent chemical bond. This type of immobilization involves surface modification of usually inert polymer supports through chemical reactions. In order to covalently immobilize the 'sensing reagent', it should essentially contain one or more (preferably one) point of attachment. The presence of more than one point of attachment leads to intrastrand cross-linking which rigidities the polymer matrix, reducing its permeability.

Figure 2A:
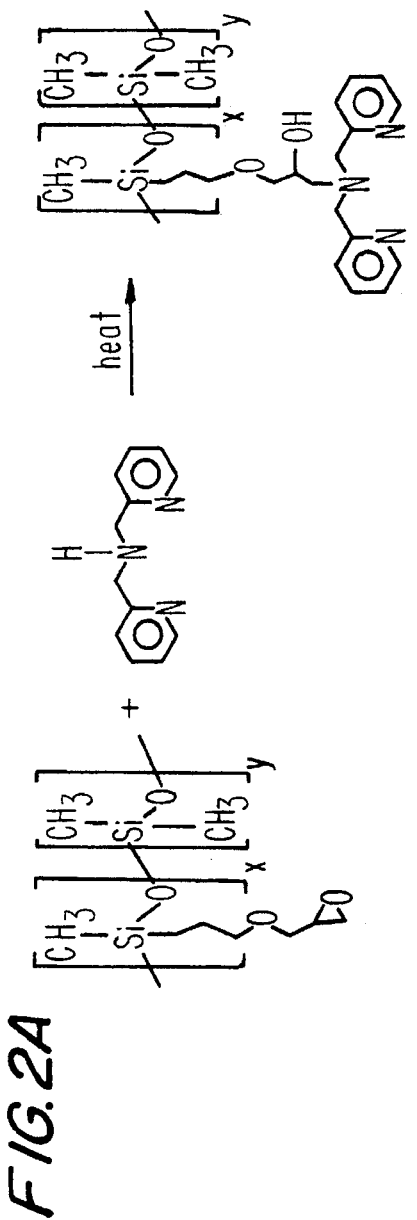
FIG. 2 shows a method used to covalently attach a ruthenium(II)-polypyridine complex to a functionalized polysiloxane.
Figure 2B:
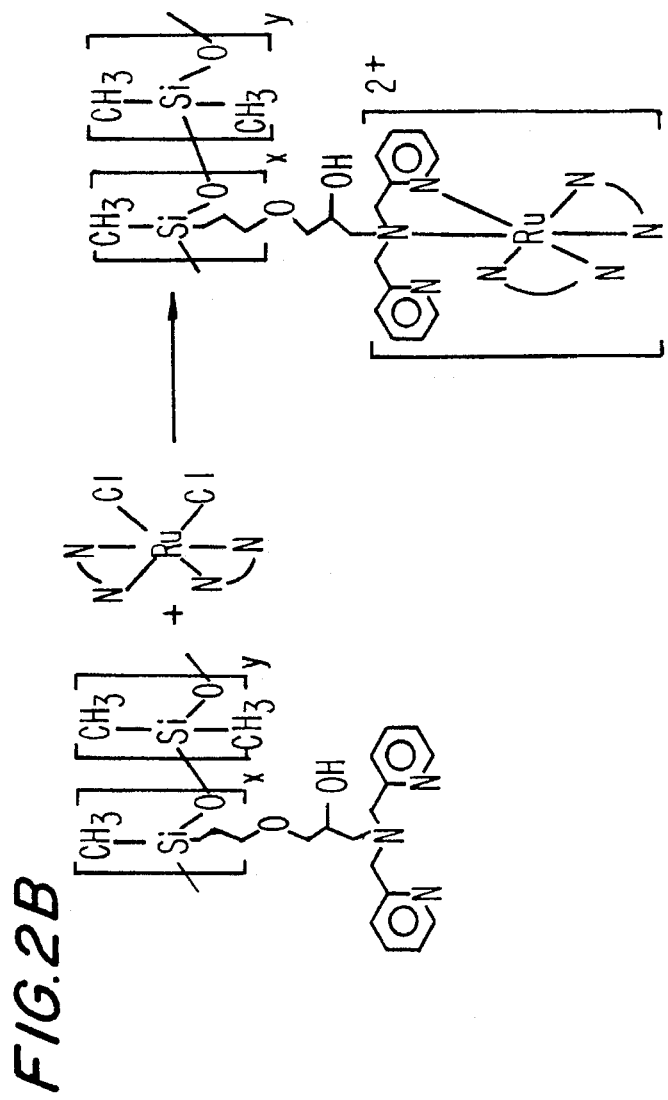

We have discovered a convenient method for covalently immobilizing luminescent metal complexes in a wide variety of polymer matrices. A typical sequence of reactions involving such an immobilization procedure is depicted in FIGS. 2 and 3. Alternatively, the tridentate ligand such as bispicolylamine can be first covalently anchored to a modified polysiloxane (FIG. 3) which on reaction with metal complexes such as [M(bpy)$_2$Cl$_2$], where bpy is 2,2'-bipyridine, or Re(CO)$_5$X (X=Cl or Br) can generate covalently or chemically immobilized luminophores, as depicted in FIG. 2. Functionalized polysiloxanes can be conveniently prepared through the modification of commercially available polysiloxanes. Covalent binding of oxygen indicators to siloxanes has been described and such gas-permeable compositions have been shown useful for fiber-optic chemical and biosensors [Hsu and Heitzmann, U.S. Pat. No. 4,712,865 (1987)].

Both low-molecular-weight and immobilized luminophores can be characterized on the basis of their optical spectra (UV/visible), photophysical (emission and excited state life time) and photochemical (luminescence quantum yields) properties. These techniques are also employed for characterizing the purity of luminophores. The purity of low-molecular weight luminophores is also checked by NMR ($^1$H and $^{13}$C) and mass (FAB$^+$) spectroscopic and chromatographic methods. A slight impurity (ca. 3 weight %) in these luminophores can lead to erroneous results. The optical, photophysical and photochemical properties of the low-molecular weight luminophores remain largely unchanged on their chemical immobilization in polymeric matrices. However, the intensities of the relevant bands in UV/visible regions of the optical spectra and their emission lifetimes are significantly attenuated. Some of the optical, photophysical and electrochemical properties of some of the low-molecular weight luminophores are summarized in Table 1.

To illustrate further the present invention, the following specific examples are given. Unless otherwise specified, all parts and percentages are by weight and all analyses are performed by standard methods used in elemental analysis, optical, emission, NMR and mass spectrometric measurements. It is to be noted that these examples are for illustrative purposes only and do not purport to be wholly definite as to condition and scope.

TABLE 1

Spectroscopic (absorption and emission) and electrochemical properties of ruthenium(II) and osmium(II) complexes.

| Complex | Absorption Spectrum$^a$ (nm) ($\epsilon \times 10^3$ Mol$^{-1}$ cm$^{-1}$) | Luminescence Emission$^b$ (nm) | Lifetime$^c$ (ns) | Reduction Potential$^d$ $E_{pa}$ (volts) | $E_{pc}$ (volts) |
|---|---|---|---|---|---|
| 1. [Ru(bpy)$_2$(bpaH]$^{2+}$2PF$_6^-$ | 470 (3.0) | 630 | 500 | | |
| | 428sh (2.3) | | | −1.30 | — |
| | 342 (3.7) | | | −1.34 | −1.43 |
| | 292 (15.0) | | | −1.58 | −1.67 |
| | 246 (7.8) | | | | |
| 2. [Ru(bpy)$_2$(beaH)]$^{2+}$2PF$_6^-$ | 476 (3.0) | 670 | — | | |
| | 428sh (2.0) | | | −1.55 | −1.67 |
| | 342 (3.3) | | | | |
| | 292 (18.0) | | | | |
| | 248 (8.4) | | | | |
| 3. [Ox(bpy)$_2$(bpaH)]$^{2+}$2PF$_6^-$ | 486 (8.9) | 724 | 50 | | |
| | 432 (6.4) | | | −1.08 | −1.18 |
| | 358 (5.7) | | | | |
| | 290 (32.2) | | | | |
| | 256 (22.3) | | | | |

$^a$In acetonitrile solution at ambient temperature;
$^b$corrected emission maxima in acetonitrile solution purged with argon;
$^c$luminescence lifetimes in deaerated acetonitrile solution at ambient temperature;
$^d$in acetonitrile solution containing 0.1M tetraethylammomium hexafluorophosphate as supporting electrolyte; potential vs. standard calomel electrode.

EXAMPLE 1

Synthesis of Metal-polypyridine Complexes

Figure 4A:
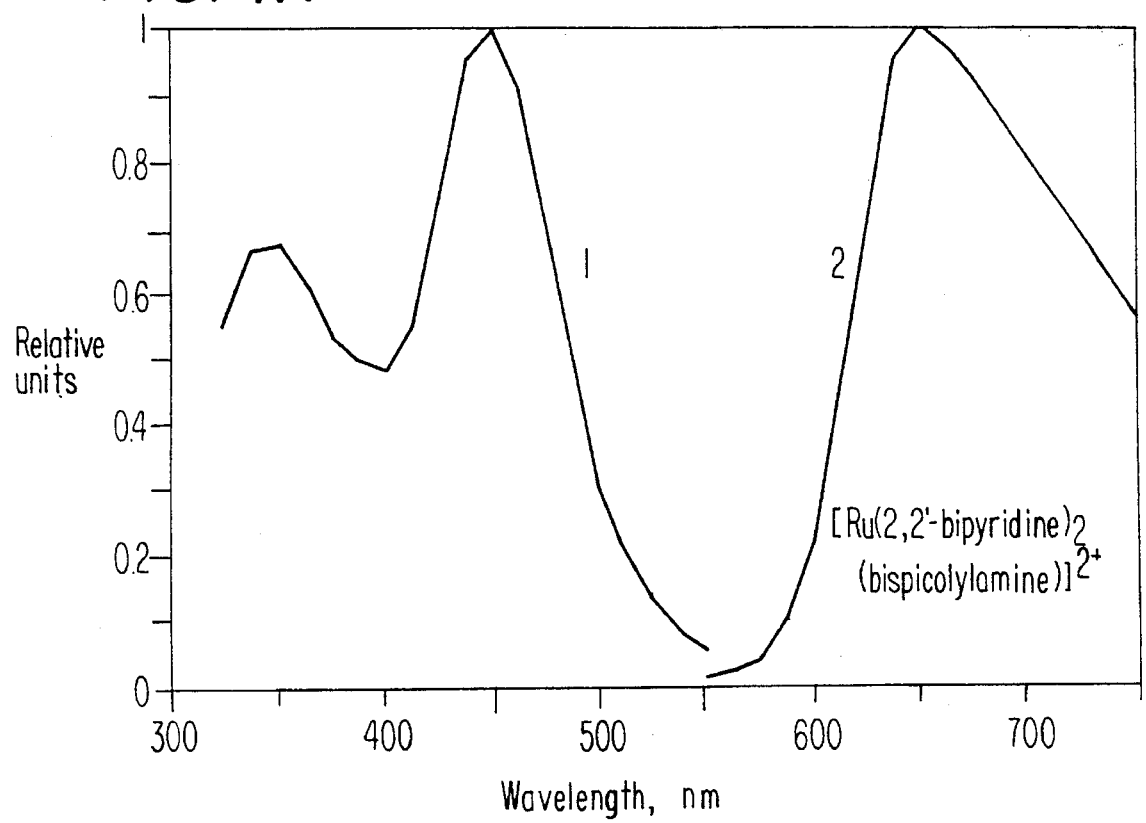
FIG. 4 depicts (1) absorption and (2) emission spectra of [Ru(2,2'-bipyridine)$_2$(bispicolylamine)]$^{2+}$ 2X$^-$ and [Ru(4,7-diphenylphenanthroline)$_2$-(bispicolylamine)]$^{2+}$2X$^-$, where X is an anion such as $PF_6^-$, $BF_4^-$ or $ClO_4^-$.
Figure 4B:
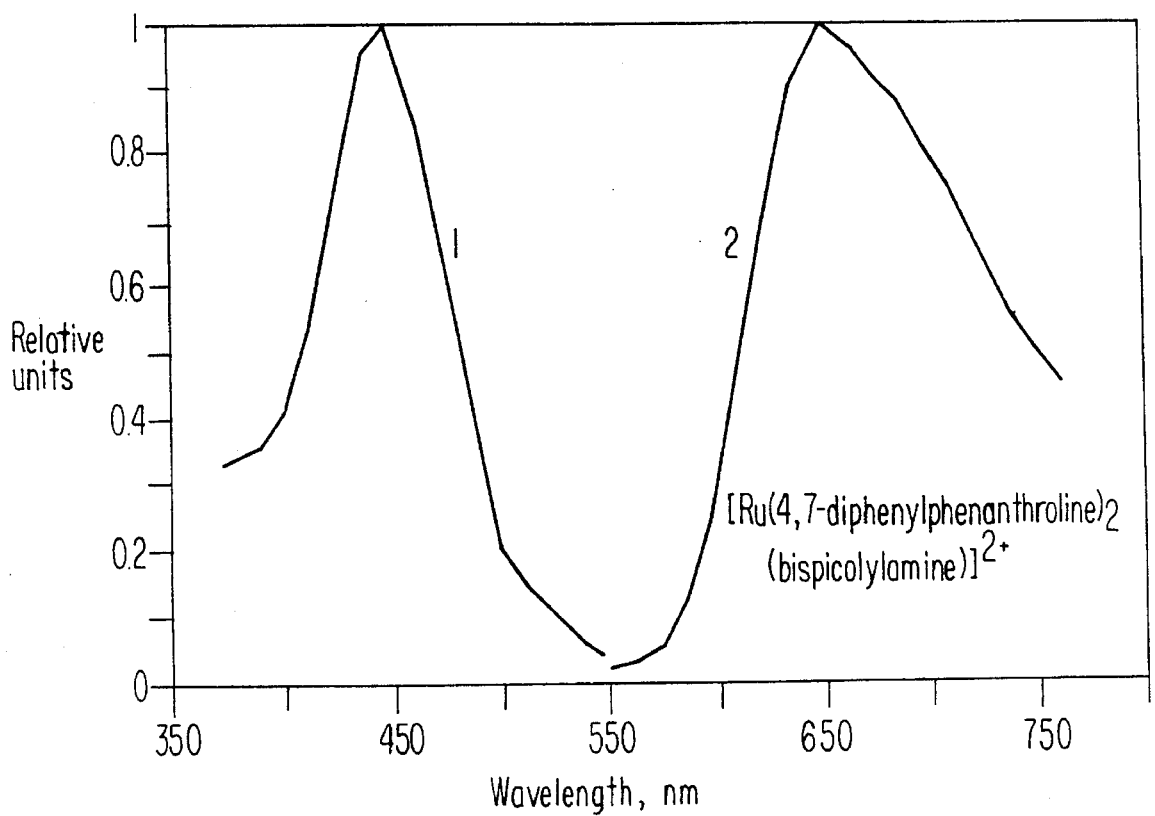
Figure 5:
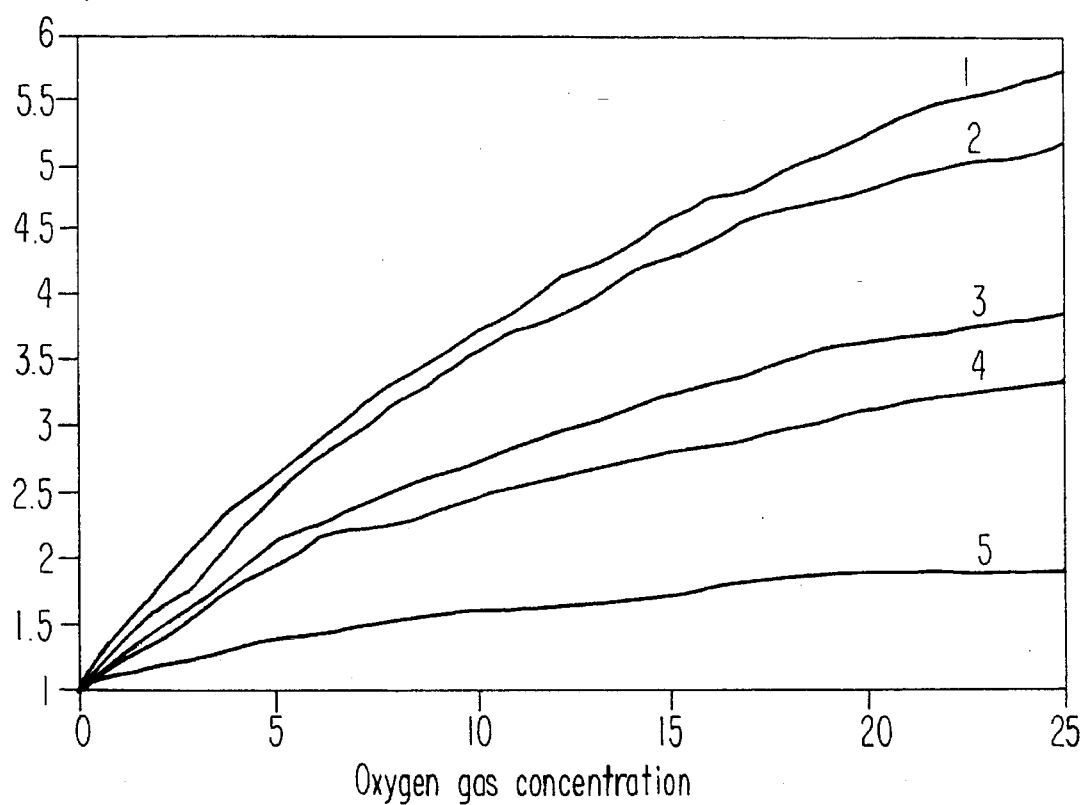
FIG. 5 shows a Stern-Volmer Plot of the quenching of the luminescence of various ruthenium(II)-polypyridine complexes by oxygen; SK-47A represents [Ru(2,2'-bipyridine)$_2$(2,2'-dipyfidylamine)]$^{2+}$2X$^-$; SK-111 represents [Ru(2,2'-bipyridine)(pyridine-4-ethylcarboxylate)$_2$]$^{2+}$2X$^-$; SK-90 represents [Ru(2,2'-bipyfidine)$_2$(bispicolylamine)]$^{2+}$ 2X$^-$; SK-dpp represents [Ru(4,7-diphenylphenanathroline)$_2$(bispicolylamine)]$^{2+}$2X$^-$; and SK-97A represents for [Ru(1,10-phenanthroline)$_2$(bispicolylamine)]$^{2+}$2X$^-$; where X$^-$ represents the counterion $PF_6^-$.
Figure 6:
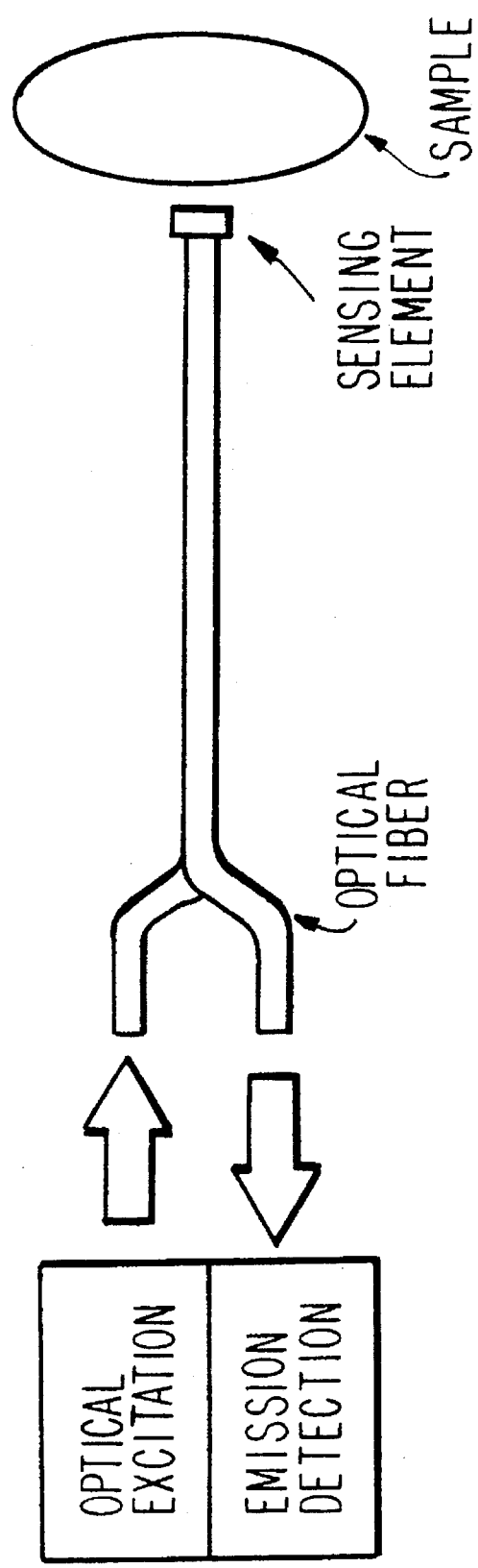
FIG. 6 shows a fiber optic sensing device in which the sensing element comprises the polymer luminopheres of the this invention.

A variety of ruthenium(II), osmium(II), or rhenium(I)carbonyl haldepolypyridine complexes, which can be chemically immobilized in a variety of functionalized polymeric matrices, were prepared by a general method. As an example, the preparation of [Ru(bipyridine)$_2$(bispicolylamine)]$^{2+}$2PF$_6^-$ is described. The starting material cis-[Ru(bipyridine)$_2$Cl$_2$].2H$_2$O was synthesized according to a published procedure [Sulliman, Saloman and Meyer, Inorganic Chemistry, 1978, 17, 3334]. cis-[Ru(bipyridine)$_2$Cl$_2$].2H$_2$O (0.15 g) was dissolved partially (or suspended) in 20 ml of 1:1 ethanol and water mixture and a 100% molar excess of the mixed ligand bispicolylamine (0.1 g) was added. The resulting mixture was deaerated by flushing with nitrogen. The mixture was refluxed while stirring under nitrogen for about 6 hours. The reaction contents were allowed to cool to room temperature for several hours and filtered to remove any unreacted residues. The clear solution was concentrated under vacuum to half its volume. The concentrated reaction mixture was filtered and to the filtrate was added a concentrated solution of ammonium hexafluorophosphate (1 gram of NH$_4$PF$_6$ dissolved in 7 ml of water). A dark orange precipitate was instantly obtained. It was successively washed with cold water, ethanol and ether. The product was dried overnight under vacuum at room temperature, yielding 0.27 g of the purified orange complex. The product was further purified by column chromatography using Sephadex LH-20 as a packing material and methanol was used as eluent. The middle dark red fraction was collected and the solid complex could either be obtained through slow evaporation of a methanol solution in a refrigerator (shiny red crystals are usually obtained by this method) or by removing the solvent under vacuum. The purified complex was obtained at ca. 76% yield. The complex was characterized on the basis of its elemental analysis, and NMR ($^1$H, $^{13}$C, and $^{31}$P), infrared, UV-visible, emission, mass spectrometric (fast atom bombardment, FAB$^+$), and photophysical (lifetimes of its excited state, $\tau$), photochemical (quantum yield of its luminescence, $\phi$) and electrochemical (cyclovoltammetry, CV) properties. The spectroscopic properties and microanalytical data for this complex and other selected complexes are given in Table 2. The absorption and emission spectra of some of these complexes is depicted in FIG. 4; the Stern-Volmer plots of the quenching of various ruthenium(II)-polypyridine complexes by oxygen are depicted in FIG. 5.

Table 2. Microanalytical and Spectroscopic Data
Microanalysis of the Complexes
[Ru(bpy)$_2$(bpaH)]$^{2+}$ Anal. Calcd for C$_{32}$H$_{29}$N$_7$P$_2$F$_{12}$Ru: C, 42.58; H, 3.24; N, 10.86. Found: C, 42.14; H, 3.12; N, 10.55. [Ru(bpy)$_2$(beaH)]$^{2+}$ Anal. Calcd C$_{34}$H$_{33}$N$_7$P$_2$F$_{12}$Ru.H$_2$O: C, 43.04; H, 3.72; N, 10.33. Found: C, 43.09; H, 3.68; N, 10.54.

[Os(bpy)$_2$(bpaH)]$^{2+}$ Anal. Calcd for C$_{32}$H$_{29}$N$_7$P$_2$F$_{12}$Os: C, 38.75; H, 2.95; N, 9.89. Found: 38.80; H, 3.05; N, 10.01

Positive Fast Atom Bombardment-Mass Spectral Data
FAB$^+$-MS (in p-nitrobenzyl alcohol): [$^{102}$Ru(bpy)$_2$(bpaH)$^{102}$Ru(bpy)$_2$(bpaH)(PF$_6$)$_3$]$^+$, m/z=1661; [Ru(bpy)$_2$(bpaH)+H (PF$_6$)$_2$], $^+$ m/z=904; [Ru(bpy)$_2$(bpaH)(PF$_6$)]$,^+$ m/z=758;
[Ru(bpy)$_2$(beaH)(PF$_6$)]$^+$, m/z=786; [Os(bpy)$_2$(bpaH)(PF$_6$)$_2$)+H]$,^+$ m/z=991;
[Os(bpy)$_2$(bpaH)(PF$_6$)]$^+$, m/z=846.

$^1$H and $^{13}$C NMR Spectral Data
$^1$H NMR data for [Ru(bpy)$_2$(bpaH)]$^{2+}$ in CD$_3$COCD$_3$:$\delta$10.088 (d, 1H, J= 8.9 Hz), 8.975 (d, 1H, 8.4 Hz), 8.750 (d, 1H, J=11.1 Hz), 8.575 (dt, 2H, J=11.1 and 6.3 Hz), 8.318 (d, 1H, J=8.1 Hz), 8,272 (d, 1H, 4.8), 8.224 (d, 1H, J=8.1 Hz), 7.969 (d, 1H, J=7.8 Hz), 7.899 (t, 1H), 7.895 (dt, 2H, J=9 and 6.3 Hz), 7.755 (t, 1H, J=7.8 Hz), 7.544 (d, 1H), 7.371 (t, 1H, J=5.1 Hz), 7.318 (d, 1H, J=4.2 Hz), 7.287 (d, 1H, J=6.3 Hz), 7.185 (dt, 1H, J=6.9 and 6.3 Hz), 7.125 (dt, 1H, J=5.7 and 4.2 Hz), 6.880 (d, 1H, J=5.4 Hz), 6.721 (dd, NH), 6.646 (dt, 1H, J=7.2 and 5.0 Hz), 6.482 (d, 1H, J=7.5 Hz), 4.662 (dd, 1H, J=4.96 and J=20 Hz), 4.2012 (dd, 1H, J=11.5 and J=15 Hz), 3.505 (dd, 1H, J$_{c,d}$=15 Hz), 3.0750 (dd, 1H, J$_{d,c}$=10.6 and J$_{d,e}$=16 Hz). $^{13}$C NMR: $\delta$160.032, 158.958, 158.404, 157.428, 154.695, 153.355, 152.684, 152.684, 152.845, 152.610, 151.127, 149.369, 149.089, 138.733, 138.272, 138.156, 137.798, 137.267, 129.092, 127.983, 127.620, 126.923, 125.766, 125.641, 125.081, 124.619, 123.986, 123.855, 123.800, 121.872, 118.224, 59.421 and 56.411 and $^{31}$p NMR: $\delta$–145.00 for PF$_6$.

EXAMPLE 2

Synthesis of Immobilized Luminophores

The chemically immobilized metal-polypyridine complexes can be prepared by two general methods. In one method, the tridentate ligand is first chemically attached to a functionalized polymer which in turn is reacted with a precursor complex, such as cis-[M(2,2'-bipyridine)$_2$Cl$_2$].nH$_2$O (M=Ru or Os) or Re(CO)$_5$Cl. In the second method, a presynthesized metal-polypyridine complex is chemically attached to a functionalized polymer, as described in example 3. For example, [Ru(bipyridine)$_2$(bispicolylamine)]$^{2+}$2PF$_6^-$ be immobilized in a polystyrene matrix according to the first method as follows: The immobilized bispicolylamine (0.5 g) was suspended in a mixture of ethanol and water (4:1, 100 ml) and to the suspension was added cis-[Ru(bpy)$_2$Cl$_2$] (0.15 g). The reaction mixture was flushed with nitrogen for 15 minutes and refluxed while stirring under nitrogen. Refluxing was continued for 36 hours when the color of the reaction mixture changed to wine-red. An excess of ammonium hexafluorophosphate (0.3 g) was added to the reaction mixture and refluxing was continued for an additional one hour. The reaction mixture was concentrated under vacuum to a small volume. The dark wine-red mass obtained was washed thoroughly with ethanol, aqueous ethanol (50%) and ether and dried under vacuum at room temperature. Yield: 0.2 g. A dilute solution of the complex in acetonitrile showed maxima at ca. 300 and 465 nm and an emission maximum was observed at 645 nm.

EXAMPLE 3

Immobilization of Luminophores

This example constitutes the second method of immobilization and is illustrated by immobilization of [Ru(2,2'-bipyridine)$_2$-(bispicolylamine)]$^{2+}$2PF$_6^-$ in polysiloxane matrix. A functionalized polysiloxane with hydroxypropyl or bromopropyl groups can be employed for the chemical immobilization of the complex described in Example 1. The functionalized polysiloxane containing bromopropyl groups (0.25 g) was dissolved in toluene and the solution was mixed with an excess of the complex [Ru(2,2'-bipyridine)$_2$(bispicolylamine)]$_{2+}$2PF$_6^-$ (0.3 g). Triethylamine (dried over KOH and distilled, 0.75 ml) was dissolved in toluene (10 ml) and added dropwise (over a period of 4 hours) to the refluxing mixture of a functionalized polysiloxane copolymer and the ruthenium complex. The reaction mixture was heated under reflux for additional 14 hours. The dark brown-red mixture was cooled and the residue obtained on filtration was thoroughly washed with water and ethanol and toluene. It was then dried under vacuum. A purified sample of 0.275 g of the immobilized complex was obtained. The infrared spectrum of the complex showed no band characteristic of the CH$_2$—Br bond vibration (ca. 1250 cm$^{-1}$), indicating the formation of a bond between the secondary amino nitrogen present in the complex and the functionalized polysiloxane (CH$_2$—N, ca. 1375 cm$^{-1}$). A thin film of the immobilized complex cast from its dilute solution in a mixture of chloroform and acetonitrile showed a rather broad band at 470 nm and its emission spectrum showed a band at ca. 640 nm.

These immobilized luminophores can be kept in water for an extended period of time (ca. polypyridine complexes detectable in water, showing their stability and non-leaching characteristics.

What is claimed is:
1. A class of polymeric luminophores comprising the structure

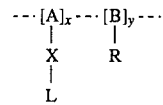

wherein:

—[A]$_x$—[B]$_y$— represents a polymer chain; A and B are independently selected from the group consisting of formulas a to i as follows:

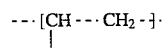 a

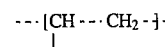 b

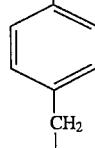

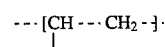 c

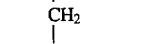 d

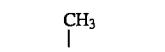 e

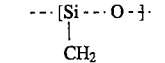 f

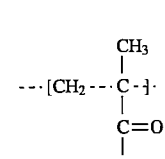

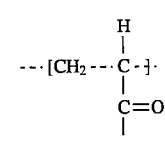 g

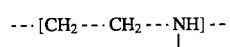 h

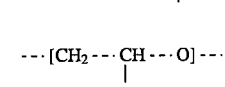 i

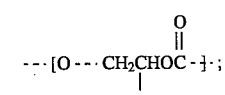

X is selected from the group consisting of —(CH$_2$)$_n$, —(CH$_2$)$_n$CH(OH)CH$_2$— and —(CH$_2$CH$_2$O)$_n$, where n is 0–10; L independently represents a luminescent platinum-metal polypyridine complex capable of having its luminescence quenched by the presence of oxygen and selected from the group consisting of the general formulas [M(N,N)$_2$(N,N,N—H)$_2$]Y$_2$, [M(N,N,N—H)$_2$]Y$_2$, [Re(CO)(N,N)(N,N,N—H)Cl], or [Re(CO)$_2$(N,N,N—H)Cl] wherein M is Ru(II) or Os(II), N,N is an α,α'-diimine bidentate ligand and N,N,N—H is a tridentate ligand of the formula P—(CH$_2$)$_s$—NH—(CH$_2$)$_t$—Q, wherein P and Q represent pyridine, quinoline, imidazole, pyrazole or triazole rings or their derivatives and s and t independently have numerical values between 0 and 3; Y is a Cl, Br, I, PF$_6$, BF$_4$, ClO$_4$, NO$_3$ or NCS anion; L is covalently bonded to X or directly to the polymer chain by substitution of a hydrogen atom bonded to of a nitrogen atom of the tridentate ligand; R independently represents hydrogen or an alkyl or aryl group; and x and y represent the number of monomer units in the polymer structure.

2. A class of polymeric luminophores according to claim 1, wherein L is covalently bonded to X or directly to the polymer chain by substitution of the hydrogen atom on the central nitrogen atom of the tridentate ligand.

3. A chemical process for preparing polymeric luminophores comprising reacting a tridentate ligand of the formula P—(CH$_2$)$_s$—NH—(CH$_2$)$_t$—Q with a polymer of the structure

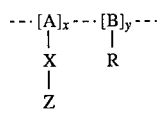

in a suitable solvent in the presence of a proton acceptor to form a product having the tridentate ligand covalently bonded to the polymer by substitution of a hydrogen atom bonded to a nitrogen atom of the tridentate ligand; and then reacting with a presynthesized N-heterocyclic complex selected from the group having the general formulas [M(N,N)$_2$Cl$_2$], [M(N,N,N—H)$_2$]Y$_2$, [Re(CO)$_5$Cl], [Re(CO)$_3$(N,N)Cl] or [Re(CO)$_2$(N,N,N—H)Cl] wherein:

—[A]$_x$—[B]$_y$— represents a polymer chain; A and B are monomer units independently selected from the group consisting of formulas a to i as follows:

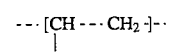 a

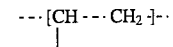 b

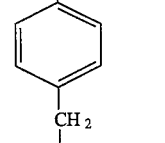

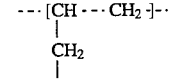 c

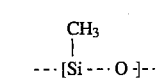 d

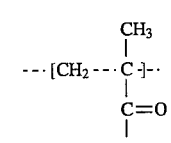 e

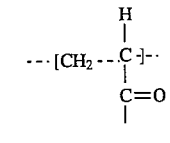 f

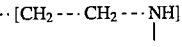 g

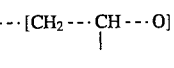 h

-continued

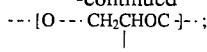       i

Z represents Cl, I, p-toluenesulfonate or methanesulfonate; X is selected from the group consisting of —$(CH_2)_n$—, —$(CH_2)_n CH(OH)CH_2$— and —$(CH_2CH_2O)_n$—, where n is 0–10; M is Ru(II) or Os(II); N,N is an $\alpha,\alpha'$-diimine ligand; N,N,N—H is a tridentate ligand of the formula P—$(CH_2)_s$—NH—$(CH_2)_t$—Q, wherein P and Q represent pyridine, quinoline, imidazole, pyrazole or triazole rings or their derivatives and s and t are integers between 0 and 3; Y is a Cl, Br, I, $PF_6$, $BF_4$, $ClO_4$, $NO_3$ or NCS anion; R independently represents hydrogen or an alkyl or aryl group; and x and y represent the number of monomer units in the polymer structure.

4. A chemical process for preparing polymeric luminophores comprising reacting a luminescent platinum-metal polypyridine complex having the general formula [M(N, N)$_2$(N,N,N—H)]Y$_2$, [M(N,N,N—H)$_2$]Y$_2$, [Re(CO)(N, N)(N,N,N—H)Cl] or [Re(CO)$_2$(N, N, N—H)Cl] with a functionalized presynthesized polymer having the structure

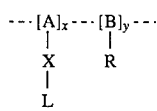

in a suitable solvent in the presence of a proton acceptor, wherein:

—[A]$_x$—[B]$_y$— represents a polymer chain; A and B are monomer units independently selected from the group consisting of formulas a to i as follows:

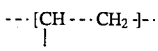                                a

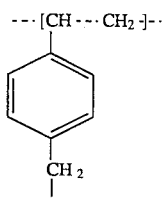                                b

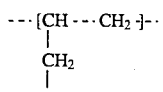                                c

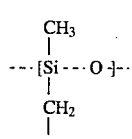                                d

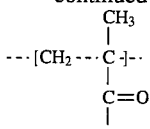                                e

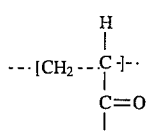                                f

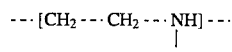                                g

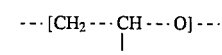                               h

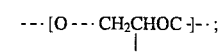                                i

Z represents Cl, I, p-toluenesulfonate or methanesulfonate; X is selected from the group consisting of —$(CH_2)_n$—, —$(CH_2)_n CH(OH)CH_2$— and —$(CH_2CH_2O)_n$—, where n is 0–10; M is Ru(II) or Os(II); N,N is an $\alpha,\alpha'$-diimine ligand; N,N,N—H is a tridentate ligand of the formula P—$(CH_2)_s$—NH—$(CH_2)_t$—Q, wherein P and Q represent pyridine, quinoline, imidazole, pyrazole or triazole rings or their derivatives and s and t are integers between 0 and 3; Y is a Cl, Br, I, $PF_6$, $BF_4$, $ClO_4$, $NO_3$ or NCS anion; R independently represents hydrogen or an alkyl or aryl group; x and y represent the number of monomer units in the polymer structure; and wherein the a luminescent platinum-metal polypyridine complex is covalently bonded to the polymer by substitution of a hydrogen atom bonded to a nitrogen atom of the tridentate ligand.

5. A fiber optic oxygen sensing device comprising: an excitation source and a luminescence detecting element at one end of an optical fiber and a polymeric luminophore according to claim 1 immobilized at the other end of the optical fiber.

6. A fiber optic oxygen sensing device for detecting analytes in a solution, said sensing device comprising an excitation source and a luminescence detecting element at one end of an optical fiber, polymeric luminophores according to claim 1 and one or more oxidase enzymes immobilized at the other end of the optical fiber forming the sensing element used to probe the sample solution.

7. A fiber optic sensing device according to claim 6, wherein said oxidase enzymes are selected from glucose oxidase, creatinine oxidase, cholesterol oxidase and alcohol oxidase.

* * * * *